US00PP19189P2

(12) United States Plant Patent
Miyazaki

(10) Patent No.: US PP19,189 P2
(45) Date of Patent: Sep. 9, 2008

(54) ***PHLOX* PLANT NAMED 'SUNPHLORAI'**

(50) Latin Name: *Phlox drummondii*
Varietal Denomination: Sunphlorai

(75) Inventor: Kiyoshi Miyazaki, Tokyo (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 11/800,784

(22) Filed: May 7, 2007

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent L. Bell
*Assistant Examiner*—S. B. McCormick-Ewoldt
(74) *Attorney, Agent, or Firm*—C. A. Whealy

(57) ABSTRACT

A new and distinct cultivar of *Phlox* plant named 'Sunphlorai', characterized by its compact and mounding plant habit; moderately vigorous growth habit; freely branching habit; lavender pink-colored flowers; freely and continuous flowering habit; and good garden performance.

1 Drawing Sheet

Botanical designation: *Phlox drummondii.*
Cultivar denomination: 'Sunphlorai'.

BACKGROUND OF THE INVENTION

The present invention relates to a new and distinct cultivar of *Phlox,* botanically known as *Phlox drummondii* and hereinafter referred to by the name 'Sunphlorai'.

The new *Phlox* is a product of a planned breeding program conducted by the Inventor in Shiga, Japan. The objective of the breeding program was to create new compact *Phlox* cultivars with attractive flower coloration.

The new *Phlox* originated from a cross-pollination made by the Inventor in June, 2002, in Shiga, Japan, of a proprietary selection of *Phlox drummondii* identified as code number 2Ph-45a, not patented, as the female, or seed, parent with a proprietary selection of *Phlox drummondii* identified as code number 2Ph-45b, not patented, as the male, or pollen, parent. The new *Phlox* was discovered and selected by the Inventor as a single flowering plant within the progeny of the stated cross-pollination in a controlled environment in Shiga, Japan.

Asexual reproduction of the new *Phlox* by vegetative cuttings in a controlled environment in Shiga, Japan since October, 2005, has shown that the unique features of this new *Phlox* are stable and reproduced true to type in successive generations.

SUMMARY OF THE INVENTION

The cultivar Sunphlorai has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunphlorai'. These characteristics in combination distinguish 'Sunphlorai' as a new and distinct cultivar of *Phlox:*

1 Compact and mounding plant habit.

2. Moderately vigorous growth habit.

3. Freely branching habit.
4. Lavender pink-colored flowers.
5. Freely and continuous flowering habit.
6. Good garden performance.

Compared to plants of the parent selections, plants of the new *Phlox* are more compact and differ in flower coloration.

Plants of the new *Phlox* can also be compared to plants of the cultivar Sunphlochebu, disclosed in U.S. Plant Pat. No. 16,723. In side-by-side comparisons conducted in Shiga, Japan, plants of the new *Phlox* and the cultivar Sunphlochebu differed in the following characteristics:

1. Plants of the new *Phlox* were smaller than plants of the cultivar Sunphlochebu.
2. Plants of the new *Phlox* had shorter lateral branches and internodes than plants of the cultivar Sunphlochebu.
3. Plants of the new *Phlox* and the cultivar Sunphlochebu differed in flower color.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph at the top of the sheet comprises a top perspective view of a typical flowering plant of 'Sunphlorai' grown in a container.

The photograph at the bottom of the sheet is a close-up view of typical flowers of 'Sunphlorai'.

DETAILED BOTANICAL DESCRIPTION

The aforementioned photographs and following observations, measurements and values describe plants grown in Shiga, Japan, under commercial practice during the summer in an outdoor nursery with day temperatures ranged from 15° C. to 33° C. and night temperatures ranging from 13° C. to 25° C. After planting, plants were pinched one time. Plants had been growing for about five months when the photographs and description were taken. In the following description, color references are made to The Royal Horticultural Society Colour Chart, 2001 Edition, except where general terms of ordinary dictionary significance are used.

Botanical classification: *Phlox drummondii* cultivar Sunphlorai.

Parentage:

*Female, or seed, parent.*—Proprietary selection of *Phlox drummondii* identified as code number 2Ph-45a, not patented.

*Male, or pollen, parent.*—Proprietary selection of *Phlox drummondii* identified as code number 2Ph-45B, not patented.

Propagation:

*Type.*—By vegetative cuttings.

*Time to initiate roots.*—About two to three weeks at 20° C. to 25° C.

*Time to produce a rooted young plant roots.*—About one to two months at 20° C. to 25° C.

*Root description.*—Fine, fibrous and fleshy; ivory white to pale brown in color.

*Rooting habit.*—Freely branching.

Plant description:

*Plant form/habit.*—Compact and mounded plant habit; outwardly spreading; vigorous growth habit. Freely branching habit; pinching enhances branching potential.

*Plant height.*—About 15 cm.

*Plant width* (*spread*).—About 20.8 cm.

*Lateral branches.*—Length: About 6 cm. Diameter: About 1.3 mm. Internode length: About 7 mm. Strength: Strong. Texture: Pubescent. Color: 144C.

Foliage description:

*Arrangement.*—Alternate, simple; sessile.

*Length.*—About 2 cm.

*Width.*—About 6.2 mm.

*Shape.*—Lanceolate.

*Apex.*—Acute.

*Base.*—Obtuse.

*Margin.*—Entire.

*Texture, upper and lower surfaces.*—Pubescent.

*Venation pattern.*—Pinnate; reticulate.

*Color.*—Developing and fully expanded leaves, upper surface: 137A; venation, 144C. Developing and fully expanded leaves, lower surface: 138B; venation, 144C.

Flower description:

*Flower type/habit.*—Single rotate hypocraterimorphous flowers arranged in terminal and axillary cymes; flowers face obliquely upward to outward. Freely flowering habit with about two to four flowers per cyme.

*Fragrance.*—None detected.

*Natural flowering season.*—Continuously flowering from spring to late autumn in Shiga, Japan. Flowers not persistent.

*Postproduction longevity.*—Flowers last about five days on the plant.

*Flower buds.*—Height: About 1.7 cm. Diameter: About 3.8 mm. Shape: Clavate. Color: N155C.

*Inflorescence height.*—About 2.5 cm.

*Inflorescence diameter.*—About 5.4 cm.

*Flower diameter.*—About 2.9 cm.

*Flower depth.*—About 1.8 cm.

*Throat diameter.*—About 1.2 mm.

*Tube length.*—About 1.6 cm.

*Petals.*—Quantity per flower: Typically five in a single whorl; petals fused at the base into a narrow tube. Length: About 1.3 cm. Lobe width: About 1.2 cm. Shape: Broadly rhombic. Apex: Cuspidate. Margin: Entire. Texture, upper and lower surfaces: Smooth, glabrous. Color: Developing and fully expanded petals, upper surface: Close to 75B; towards the base, 78B; throat, close to 75B. Developing and fully expanded petals, lower surface: Close to 76C; tube, N155C.

*Sepals.*—Quantity per flower: Typically five in a single whorl, fused at base; tubular in shape. Length: About 2.4 mm. Width: About 6 mm. Shape: Lanceolate. Apex: Acute. Margin: Entire. Texture, upper and lower surfaces: Smooth, glabrous. Color, upper and lower surfaces: 144B.

*Peduncles.*—Length: About 7.4 mm. Diameter: About 0.9 mm. Texture: Pubescent. Color: 144C.

*Pedicels.*—Length: About 3.2 mm. Diameter: About 0.6 mm. Texture: Pubescent. Color: 144C.

*Reproductive organs.*—Stamens: Quantity per flower: Typically five. Stamen length: About 8 mm to 12 mm. Anther shape: Linear. Anther size: About 2 mm by 0.8 mm. Anther color: 14A. Pollen amount: Moderate. Pollen color: 15A. Pistils: Quantity per flower: One. Pistil length: About 4 mm. Stigma shape: Transversely ellipsoidal. Stigma color: 2B. Style color: 2C. Ovary color: 144B.

*Seed/fruit.*—Seed and fruit development have not been observed.

Disease/pest resistance: Plants of the new *Phlox* have not been noted to be resistant to pathogens and pests common to *Phlox*.

Garden performance: Plants of the new *Phlox* have been observed to have good garden performance and tolerate rain, wind and temperatures from about 0° C. to about 35° C.

It is claimed:

1. A new and distinct *Phlox* plant named 'Sunphlorai' as illustrated and described.

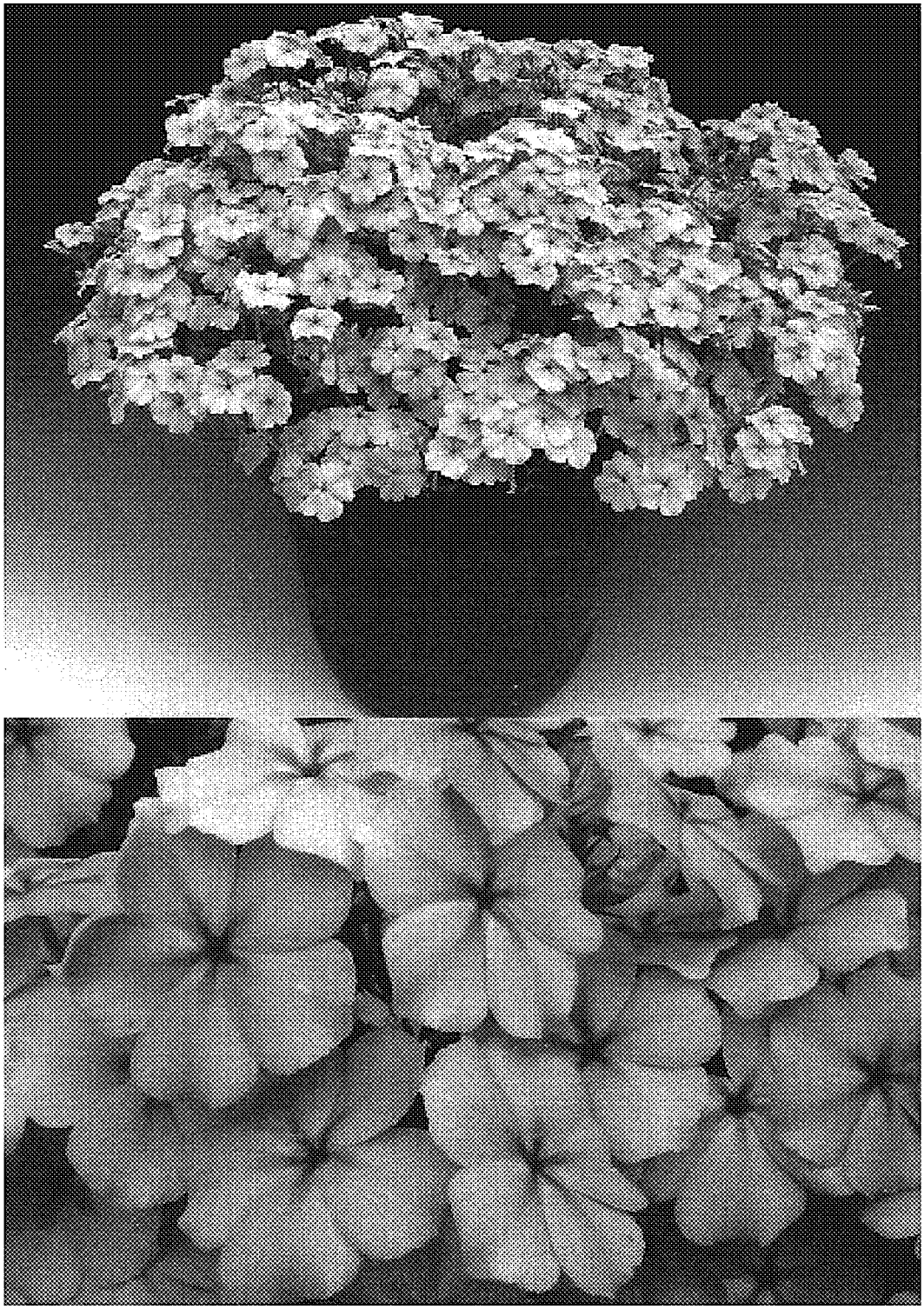

* * * * *